United States Patent
Duee et al.

(10) Patent No.: US 6,191,332 B1
(45) Date of Patent: Feb. 20, 2001

(54) METHOD AND APPARATUS FOR DEHYDROGENATING ALIPHATIC HYDROCARBONS TO OLEFINIC HYDROCARBONS

(75) Inventors: Didier Duee, Rueil Malmaison; Larry Mank, Orgeval; Pierre Renard, Saint Nom la Breteche; Jean-Piere Burzynski, Lyons; Gerard Leger, Ecully; Philippe Vacher, Vienne; Ari Minkkinen, Saint Nom la Breteche, all of (FR)

(73) Assignee: Institut Francais du Petrole, Rueil-Mailmaison Cedex (FR)

( * ) Notice: Under 35 U.S.C. 154(b), the term of this patent shall be extended for 0 days.

(21) Appl. No.: 09/028,114

(22) Filed: Feb. 23, 1998

Related U.S. Application Data

(63) Continuation of application No. 07/878,834, filed on May 6, 1992, now abandoned.

(30) Foreign Application Priority Data

May 6, 1991 (FR) .................................................. 91 05671
May 6, 1991 (FR) .................................................. 91 05673

(51) Int. Cl.[7] .......................... C07C 5/327; C07C 5/373; G05D 23/00; B01J 8/04; B01J 10/00
(52) U.S. Cl. ......................... 585/654; 585/911; 585/921; 585/924; 422/109; 422/197
(58) Field of Search ..................................... 585/654, 648, 585/911, 921, 924; 422/109, 197

(56) References Cited

U.S. PATENT DOCUMENTS

| 4,513,162 | * | 4/1985 | Al-Muddarris | 585/654 |
| 4,704,497 | * | 11/1987 | Gottlieb et al. | 585/654 |
| 4,996,387 | * | 2/1991 | Gerhold et al. | 585/654 |

FOREIGN PATENT DOCUMENTS

| 0252356 | * | 1/1988 | (FR) | C10G/9/20 |

* cited by examiner

*Primary Examiner*—Marian C. Knode
*Assistant Examiner*—Thuan D. Dang
(74) *Attorney, Agent, or Firm*—Millen, White, Zelano & Branigan, P.C.

(57) ABSTRACT

The specification describes a method and a fixed bed apparatus for producing olefinic hydrocarbons from a charge of saturated aliphatic hydrocarbons with 2 to 20 carbon atoms and hydrogen in a chamber 1 comprising a plurality of parallel tubes 3 filled with a catalyst and arranged in rows. A so-called reaction phase and a catalyst-regenerating phase are carried out in the tubes of the chamber. The tubes are heated by appropriate radiant heating means 6, arranged in layers substantially perpendicular to the tubes. These layers heat a first part of the tubes (at the feed side) with a heat flux greater than the mean heat flux of the chamber and a second, subsequent part with a mean flux no more than equal to the mean heat flux, so that the isothermicity of the catalyst is substantially maintained, using appropriate control means.

25 Claims, 2 Drawing Sheets

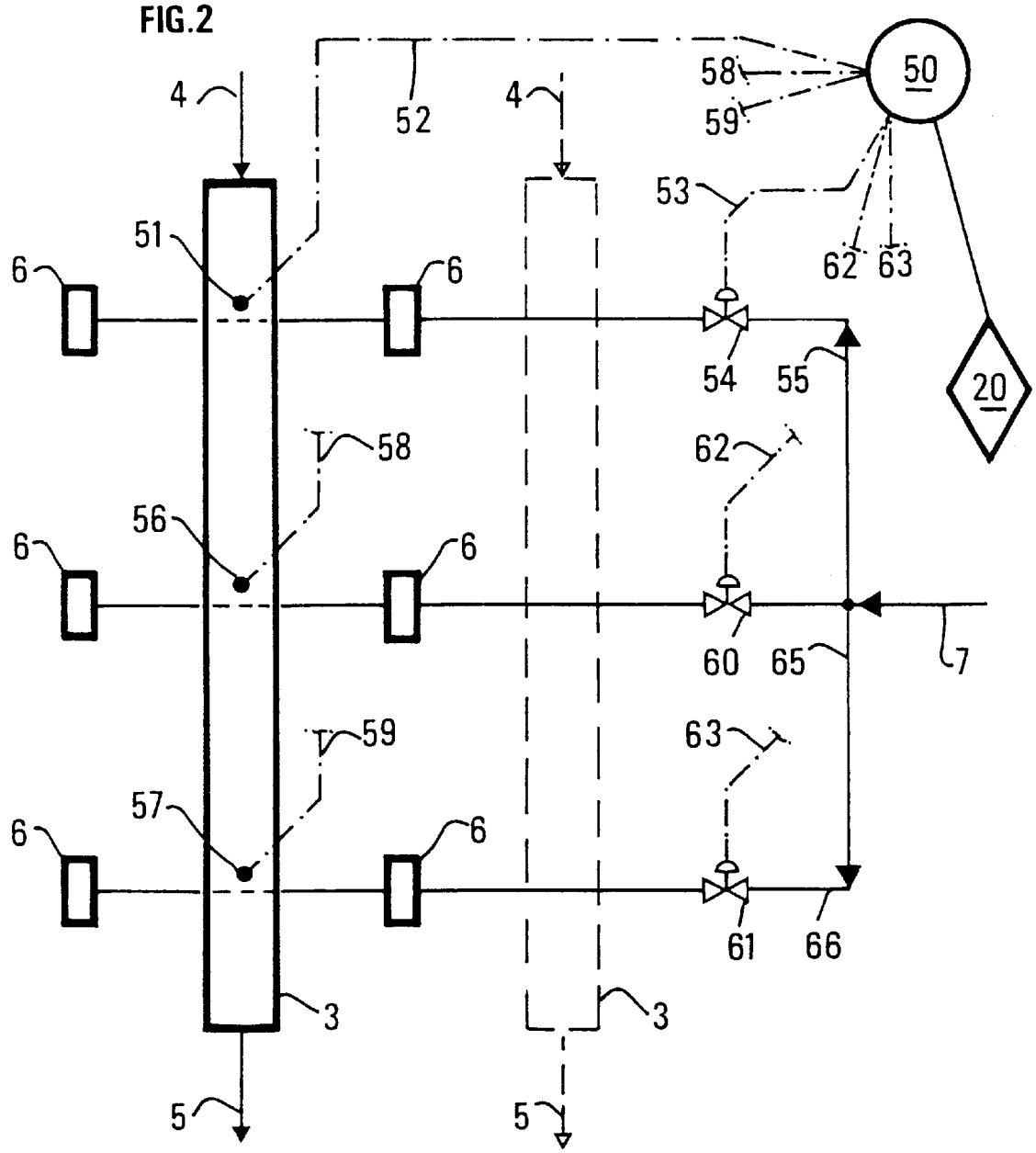

METHOD AND APPARATUS FOR DEHYDROGENATING ALIPHATIC HYDROCARBONS TO OLEFINIC HYDROCARBONS

This is a continuation of application Ser. No. 07/878,834 filed May 6, 1992 now abandoned.

The invention concerns a method and apparatus for converting hydrocarbons, particularly to produce olefinic hydrocarbons with at least one double bond, from a charge of aliphatic hydrocarbons with 2 to 20 carbon atoms in the presence of a catalytic composition. The conversion entails an endothermic reaction to produce hydrocarbons, followed by an exothermic reaction to regenerate the catalyst with coke deposited on it. The invention also concerns the use of the apparatus. It more particularly concerns the synthesis of isobutene, which is used especially in the preparation of MTBE (methyl tertiarybutyl ether) with a view to improving the octane number of petrols.

The upgrading of cuts, particularly aliphatic ones with a low boiling point such as the C4 cut from steam cracking or catalytic cracking and the LPGs, explains the importance which may be attached to using hydrocarbon conversion methods which are efficient, selective and economic and which also contribute to the formation of hydrogen.

The technological background is illustrated by patent JP-A-63197534.

The reaction producing olefinic hydrocarbons has been described especially in U.S. Pat. No. 4,704,497. It uses a catalyst containing alumina.

The basic processes used in converting aliphatic hydrocarbons to olefinic hydrocarbons are chiefly dehydrogenation of paraffins. Taken as a whole, the reaction is endothermic, the reaction speed is sensitive to temperature variations and the successive reactions are accompanied by deposition of coke on the catalyst and reduction of the metal oxides contained in the catalyst, with the result that the catalyst is deactivated very rapidly and the cycle is shortened.

One of the problems to be solved is thus how to ensure uniform heating of the reaction zone in the region of 500 to 600° C. so as to obtain the flattest possible temperature profile therein, with the knowledge that the catalyst is sensitive to a temperature increase and may be destroyed when the critical temperature is exceeded.

It has in fact been found that the heat requirement does not remain constant as the endothermic reaction producing olefinic hydrocarbons progresses.

Another problem to be solved relates to regeneration of the catalyst: it must be rapid and of variable frequency according to the reaction temperature, which is directly dependent on the charge to be treated, and thus according to the quantity of coke deposited. Regeneration is generally carried out, e.g., every ten hours. It must be gentle enough to maintain the performance of the catalyst and to minimize its replacement rate.

During the used catalyst regenerating phase it is moreover preferable to reach the coke combustion temperature as rapidly as possible, in order to maintain a substantially constant temperature level right along the tube and hence a homogeneous level of activity, in order to keep the catalyst active for as long as possible.

It has been recommended that the regenerating gases should be introduced at a very high temperature level (600–700° C.), so as not to overcool the catalyst at the reactor inlet and so as to compensate for the shortage of coke required to initiate the reaction.

It has also been recommended that a gaseous or liquid fuel should be added, in a large enough quantity to raise the temperature of the regenerating gas before it enters the reactor.

This solution has the disadvantage of initiating cracking of the hydrocarbon molecules and fostering the appearance of undesirable byproducts.

The object of the invention is to deal with the problems raised above so as to improve the rates of conversion to olefinic hydrocarbons and the durability of the catalyst.

More particularly, the invention concerns a method of producing olefinic hydrocarbons from a charge including aliphatic hydrocarbons with 2 to 20 carbon atoms which can be dehydrogenated in at least one reaction chamber, the chamber having a plurality of substantially parallel tubes arranged in rows and containing a fixed bed of catalyst, characterize in that:

a) a reaction phase producing olefinic hydrocarbons is carried out, during which the possibly preheated charge is circulated in the tubes containing the catalytic composition under appropriate conditions, and an effluent rich in olefinic hydrocarbons is collected:

b) a phase of purging the tubes with at least one appropriate gas is carried out, after the reaction phase and after a catalyst-regenerating phase defined below, and a purge effluent is collected:

c) and a phase of regenerating the catalyst is carried out in the tubes of the chamber under appropriate regenerating conditions, the catalyst being in a fixed bed and having had coke deposited on it during the reaction phase, and a regeneration effluent is recovered, the method further being characterize in that the tubes are heated during the reaction phase by a plurality of appropriate radiant heating means arranged in layers which are substantially parallel, independent of one another and substantially perpendicular to the tubes, the heating means being adapted to heat a first part (the feed side) of the tubes with a heat flow greater than the mean heat flow of the reaction chamber necessary for the production of hydrocarbons, and adapted to heat a second part of the tubes, downstream of the first part, with a heat flow no more than equal to said mean heat flow, so that the isothermicity of the catalyst is substantially maintained, and any combustion fumes emanating from the heating means eventually discharged from the chamber.

The word "charge" refers to a mixture of aliphatic hydrocarbons and hydrogen or steam.

The term "olefinic hydrocarbons" refers to a hydrocarbon with at least one double bond.

One feature of the process is that 1 to 50% of the length of the reaction tubes, at the feed side, may be heated with a heat flow from 101 to 500% of the mean heat flow of the reaction chamber, and the remaining part of the tubes with a heat flow from 10 to 100% of the mean heat flow.

The mean heat flow of the chamber is defined by the ratio of the power absorbed by the tubes of the chamber for a given reaction to the total external area of the tubes.

From 1 to 40% and preferably 1 to 35% of the length of the reaction tubes at the feed side may advantageously be heated with a heat flow from 120 to 300% and preferably 150 to 200% of the mean heat flow, and the remaining part of the tubes with a heat flow from 20 to 85% and preferably 40 to 75% of the mean heat flow.

Under these conditions the temperature profile right along the tube is substantially flat, allowing for a higher heat demand in the first part of the tube than in the remaining part. In this case use of the catalyst may be optimized relative to the quasi maintenance of its activity for the longest possible time.

The heating means used may advantageously be those described in U.S. Pat. No. 4,664,620, comprising burners of substantially cylindrical, elongated shape with a matrix of ceramic fiber, which burn a mixture of gaseous fuel and air, without a flame, in the interstitial spaces between the fibers and transfer the heat by radiation. The use of these ceramic fiber burners is thus a subject of the invention.

They further have the advantage of liberating little $NO_x$ and little CO and hydrocarbon during combustion. Their use is also very flexible: the quantity of heat liberated may be controlled and may preheat the charge and the purging and regenerating gases.

In addition they have very little inertia. This is important in the event of inopportune termination of the feeding of the charge, or an excessive coke deposit on the catalyst which may interrupt the feeding of the charge.

Another feature of the process is that a purging phase is normally carried out in between the phase producing olefinic hydrocarbons and the phase regenerating the used catalyst. For this purpose the feeding of the charge to the tubes is reduced or stopped and the tubes are purged at least once with an inert gas such as nitrogen, under flow and temperature conditions such that the temperature of the catalyst remains substantially constant. This purging phase may be repeated in between a regenerating phase and a reaction phase, with the result that the catalyst is in an inert gas atmosphere before being put into contact either with oxygen in its regenerating phase or with hydrocarbons during the reaction phase.

During the purging phase it is however preferable to keep the catalyst at a substantially constant temperature right along the reaction tubes, with a view to either subsequent regeneration of the catalyst or a phase of dehydrogenating the hydrocarbon charge. This temperature may be controlled and is preferably as close as possible to that of the reaction phase and that of the regenerating phase, in order to avoid discontinuities of profile which would adversely affect the properties of the catalyst and fatigue the equipment.

Moreover if heating is maintained during the purging period, this helps to stabilize preheating of the charging, purging or regenerating gas at the highest possible level.

Another feature of the process is that the catalyst regenerating phase is generally carried out by injecting the preferably heated inert gas and at least one gas containing 0.01 to 5% by volume, preferably 0.4 to 0.8% by volume of molecular oxygen into the tubes and heating 1 to 50%, preferably 1 to 35% of the length of the tubes at the feed side with a heat flow from 5 to 100% of the mean heat flow of the reaction chamber used during the reaction phase, under conditions such that the exothermicity of the coke combustion reaction is controlled and the temperature of the catalyst is kept substantially constant along the reaction tubes.

The catalyst regenerating phase may also be carried out in a plurality of successive stages:

a) combustion by means of at least one gas containing molecular oxygen in the proportions given above and at a temperature generally from 400 to 650 and advantageously from 500 to 550° C., under the above-mentioned operating conditions;

b) oxychlorination by means of a gas simultaneously containing molecular oxygen and chlorine or a chlorine compound, preferably in the presence of moist air, chlorine and nitrogen at a temperature generally from 450 to 550° C.;

c) and a possible final calcination by means of a gas generally containing a higher concentration of oxygen, particularly if oxychlorination has been effected with moist air.

The passage from the regenerating phase to the hydrocarbon producing phase is obviously made generally by carrying out a purging phase, e.g. as described above. This brings the catalyst from an oxidizing atmosphere to an inert atmosphere and is advantageously followed by reduction in $H_2$ before the beginning of the reaction phase.

In a preferred embodiment of the method of the invention, the reaction chamber may comprise at least one module which has two sets of tubes disposed in substantially parallel rows. The reaction phase generally takes place in one of these sets of tubes while the catalyst regenerating phase is taking place in the other. When regeneration is substantially over, after the purging period, the tubes which were previously used for regeneration may then be used as the reactor producing olefins.

This alternating action, produced by a set of valves controlled by appropriate means, is found to be very flexible.

The homogeneous temperature of the bed of catalyst during the hydrocarbon producing phase is an advantage when the catalyst is regenerated in the same tubes. The profile of the coke deposited along the tube is substantially constant and hence the regenerating temperature is more uniform.

The method thus described reduces the time of passage between the reaction cycle and the regeneration cycle, since the temperature is substantially the same in both cases and the method is carried out in the same tubes.

The dehydrogenation reaction generally takes place at an absolute pressure of 0.2 to 20 bar (1 bar=0.1 MPa) and a temperature of 500 to 800° C. according to the nature of the charge. The temperature is advantageously from 600 to 700° C. for propane and 550 to 650° C. for the cut containing isobutane, at a preferred absolute pressure of 1 to 3 bar. The recommended space velocities are normally 0.5 to 20 $h^{-1}$ and preferably 1.5 to 2.5 $h^{-1}$.

The catalyst may be that described, e.g., in U.S. Pat. No. 4,806,624. It may, for example, comprise an amorphous or crystalline carrier, preferably alumina, with a specific surface area of about 25 to 500 m2/g.

It advantageously comprises at least one precious metal from Group VIII of the Periodic Table, i.e., selected from an the group formed by ruthenium, rhodium, palladium, osmium, iridium and platinum.

It further advantageously comprises at least one promoter selected from the elements of Group VII B, e.g., manganese and rhenium, preferably rhenium, or from Group IV A, preferably tin.

The catalyst may be neutralized by at least one compound containing an alkali metal or alkaline earth metal element, advantageously calcium, strontium, barium and radium and preferably potassium.

The catalyst will be selected according to the charge to be treated.

The catalyst used may equally be a crystalline zeolite such as natural or synthesized mordenites.

These zeolites may advantageously contain at least one of the above-mentioned metals.

Zeolites which have been synthesized in a fluoride medium either with or without metal may also be used, the metal being in the framework or outside it.

The hydrocarbon charge may comprise saturated or unsaturated hydrocarbons with only one double bond, advantageously with 2 to 6 carbon atoms. These hydrocarbons may be propane, n-butane, n-pentane, isomers of butane and pentane or mixtures thereof. They may also be, e.g., propene, butenes and pentenes and are generally products resulting from dehydrogenation of the original charge, which are recycled.

The hydrocarbons are put into the fixed bed either pure or diluted with an inert gas.

Hydrogen emanating from recycling of the final product separated, or steam, is associated with these hydrocarbons in the charge.

The hydrogen is recycled in such a way that the molar ratio of $H_2$ to hydrocarbons is from 1 to 10, preferably 2 to 5. Similarly the molar ratio of $H_2O$ to hydrocarbons may be from 1 to 10 and preferably 2 to 5.

Excellent results have been obtained with a charge comprising hydrogen and isobutane emanating from a C4 cut from steam cracking or catalytic cracking, or from an LPG cut in which a large quantity of butanes are found.

The charge may, for example, be of the following composition:

| | |
|---|---|
| isobutane | 20–93% |
| n-butane | 5–78% |
| C3 + C5 | 2–5% |

The arrangement according to the invention thus enables charges of variable composition to be accepted very rapidly, through easy control of the temperature of the chamber. It also allows the catalyst regeneration rate to be adjusted according to the heat balance and according to the quantity of coke on the catalyst, which depends chiefly on the nature of the charge. Another advantage is due to the fact that the charge, purging gases and regenerating gases may be preheated, particularly in the convection section for the combustion fumes from the heating means, and introduced at an appropriate temperature.

Operating conditions are generally optimized so as to convert 10 to 70% and preferably 30 to 50% of the charge per pass, with a selectivity for olefins of at least 85% and preferably 90 to 95%. The yield of (iso and n) olefins produced per pass is generally over 20% and preferably from 30 to 50% by weight.

The non-converted part of the charge may be recycled when the effluents have been removed.

Higher conversion rates may be obtained with heavier charges: for example, at least 95%.

Regeneration is generally effected at a temperature from 400 to 650° C. and preferably from 500 to 550° C.

The method of the invention may be carried out in a hydrocarbon converting apparatus provided with at least one chamber 1 containing at least one reactor 2, in which the endothermic reaction takes place and which has a plurality of tubes 3, substantially parallel with one another and fed in parallel, the tubes being filled with at least one catalyst in a fixed bed, charge-feeding means 4 connected to one end of the tubes and effluent-recovering means 5 connected to the other end of the tubes, the tubes being disposed in substantially parallel rows and being heated under appropriate conditions by a plurality of radiant heating means 6 such as ceramic fiber burners, which are arranged in substantially parallel layers, independent of one another and substantially perpendicular to the tubes, the heating means having means 7 for feeding fuel and oxidant and means 16 for discharging combustion fumes connected to said reactor, the apparatus further comprising means 9, 28 for regenerating the spent catalyst, including means for purging the tubes with at least one appropriate gas, means 9a, 9b for feeding at least one regenerating gas and means 10, 32 for discharging the regeneration effluent, adapted to regenerate the spent catalyst in the tubes, these regenerating means being connected to the tubes, and alternate displacement means 20 adapted to connect the tubes alternately to the charge feeding means 4 and effluent recovery means 5, then to the catalyst-regenerating means 9, 28, the apparatus further comprising means 50 for controlling and regulating the temperature of the tubes, connected to the layers of heating means.

The heating means generally comprises a fuel and oxidant feed and means for discharging combustion fumes, connected by appropriate passages to a convection chamber which is itself connected to a chimney. The convection chamber may have a heat exchanger adapted to preheat the charge and the purging and regenerating gases.

The tubes used within the framework of the apparatus are generally from 2 to 20 m long. They may be cylindrical or annular. In the case of annular tubes there is a peripheral annular portion containing the catalyst and a central portion.

In a first alternative embodiment the charge may be put into the annular portion at one end and move axially through it, and the effluent may move in the other direction through the central part of the tube, where it is recovered at the other end located at the same side of the tube. In this case the tubes are heated at their periphery by the heating means.

In a second preferred alternative embodiment the charge may be put into the annular portion at one end, move axially through it and be discharged at the opposite end. The central portion of the tubes is partly occupied by the heating means, which are advantageously cylindrical, either joined or separate and adapted to heat the interior of the tubes, i.e., the annular portion containing the catalyst, by the method described above, the feeding of the burners and discharge of the combustion fumes taking place at the same side, the side where the hydrocarbon effluent comes out. The distance between the burners and the inner wall of the tubes is normally from 0.2 to 10 times the annular thickness containing the catalyst. These tubes are advantageous by reason of their large capacity and their compactness in reactors.

In the case of cylindrical tubes their inside diameter is from 10 to 200 mm. They are arranged in substantially parallel, advantageously vertical rows. Each row may contain one or more lines of tubes. The distance between the axis of each tube is generally from 1.5 to 6 times its outside diameter, and the burners are arranged at the periphery of the tubes as a general rule.

Another feature is that the apparatus normally comprises regenerating- means adapted to regenerate the spent catalyst in the same tubes as where the olefin-producing reaction took place. These regenerating means generally have a regenerating gas feed at one end of the bundle of tubes and discharge means for the regeneration effluent at the other end. The latter end may be located at the same side, e.g. with the annular tubes.

The apparatus may also comprise means adapted to connect the reaction tubes alternately to the regenerating means then to the means for carrying out the reaction, and particularly to connect one end of the tubes to the charge-feeding means and the other end to the means for discharging the effluent produced; in the case of annular tubes this end may be at the same side.

In a preferred embodiment the apparatus may comprise at least one chamber with a first reactor containing a plurality of reaction tubes and a second reactor provided with a plurality of regenerating tubes adapted to regenerate the catalyst; the first and second reactor communicating through at least one passage 14, 15 with a convection section which is connected to the outside by appropriate means (chimney); the regenerating tubes being connected at one end to a regenerating gas feed and at the other end to means for discharging a regeneration effluent; and further comprising alternate displacement means adapted to connect the reaction tubes alternately to the charge-feeding means and effluent-recovery means then to the regenerating gas feed and the means for discharging the regeneration effluent; the alternate displacement means being adapted further to connect the regenerating tubes alternately to the regenerating gas feed and regeneration effluent discharge then to the charge-feeding means and the means for recovering the olefinic hydrocarbon effluent; the reaction tubes operating in the so-called reaction phase while the regenerating tubes operate in the so-called regeneration phase during a first stage, and the reaction tubes then becoming regeneration tubes while the regeneration tubes become reaction tubes during a second stage.

The design technology is very flexible owing to the modular nature of its application, and may be adapted either to large or small capacities. The flexibility with which the heating can be used at short notice is an additional asset.

Another feature of the apparatus is that the control and regulation means may comprise at least one temperature probe connected to said first portion of the tubes, and at least one other temperature probe connected to the second, subsequent portion of the tubes, the two probes transmitting signals; and processing and control means adapted to receive the signals, compare them with reference values and transmit data through other signals which can control the means for heating the first and second portions of the tubes.

BRIEF DESCRIPTION OF THE DRAWINGS

The invention will be understood better if the accompanying drawings are studied. These illustrate the method and apparatus of the invention diagrammatically, and in them:

FIG. 2 shows the means for heating the tubes and the control and regulation means which control them.

DETAILED DESCRIPTION OF THE DRAWINGS

Figure 1:
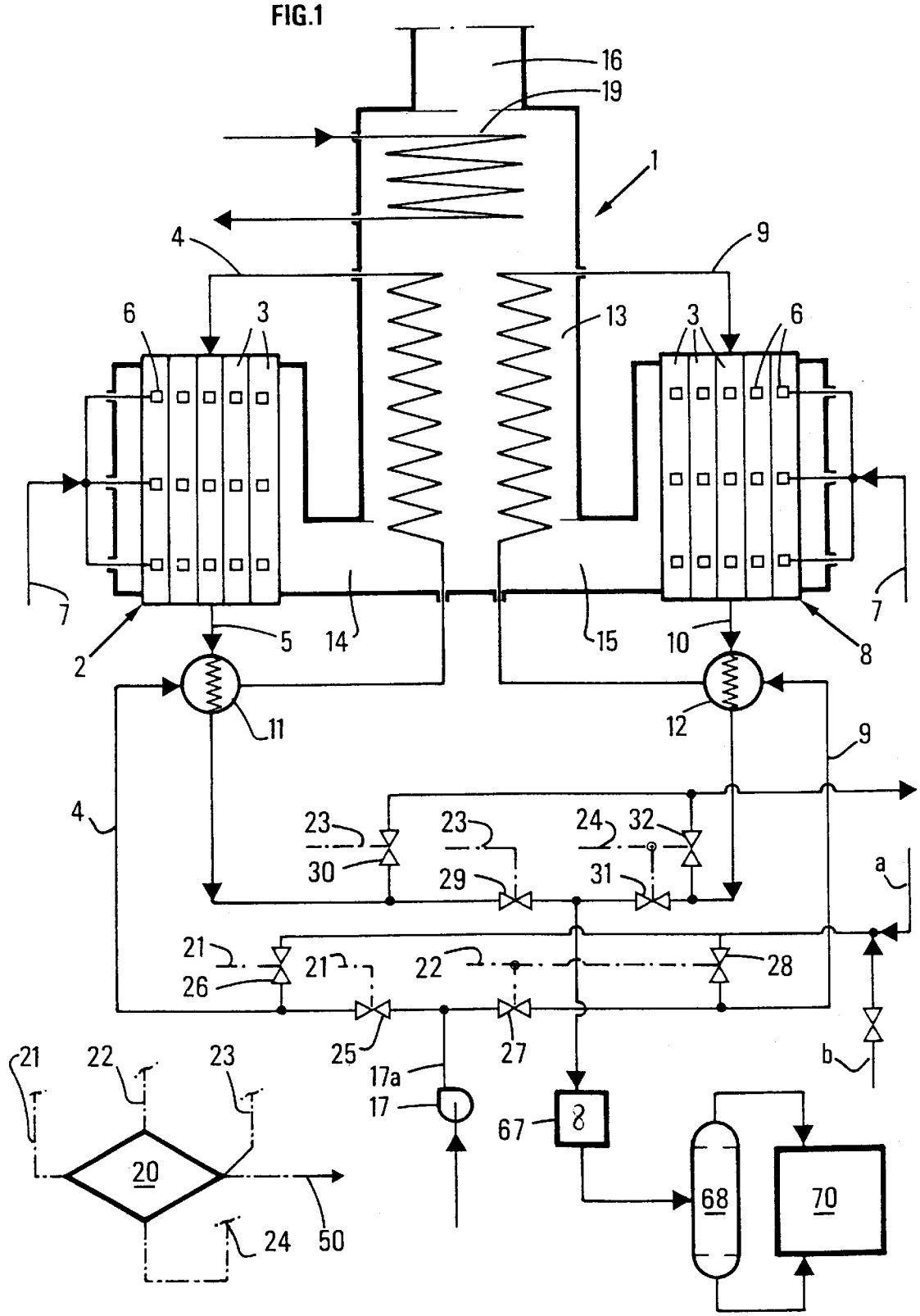
FIG. 1 is a longitudinal section through the reaction chamber, containing a reaction section and a regeneration section separated by a convection chamber.

Referring now to FIG. 1, a reaction chamber 1 with walls clad with an insulating material comprises a reactor 2 provided with a plurality of stainless steel tubes 3 of substantially cylindrical shape, which contain a fixed bed of a catalyst adapted to produce mono or diolefinic hydrocarbons. The tubes are spaced apart by a length equal to about twice their diameter, measured from the axis. They are substantially vertical and are arranged in substantially parallel rows containing two lines of preferably staggered tubes. A plurality of elongated, substantially cylindrical burners 6 with a ceramic fiber matrix are located between the rows. They can burn a mixture of gaseous fuel and air, supplied by a feed 7, without a flame. The burners are arranged in substantially parallel layers which are independent of one another and substantially perpendicular to the reaction tubes. The layers may comprise one or more burners, and the distance between burners is generally from 0.5 to 2.0 m. The distance between burners and tubes is generally from 0.2 to 0.8 m, advantageously from 0.3 to 0.5 m. These radiant burners are adapted to heat a first portion of the tubes (at the feed side) with a heat flow of about 180% of the mean heat flow of the chamber over a length of about 30% of the length of the tubes, which may be up to 8 m. The remaining part of the tubes is heated with a heat flow equal to about 70% of the mean heat flow. Under these conditions the reaction may be started instantly and it is not necessary to apply too much preheating to the charge, which would be in danger of cracking.

The combustion fumes from the burners are discharged through a passage 14 to a convection section 13 in which the charge may be preheated. Heat recovery means 19 may also be incorporated there. The fumes are discharged through a chimney 16.

The tubes of the reactor are fed in parallel with a charge comprising aliphatic hydrocarbons, e.g. a C4 cut, which is supplied through lines 17a and 4 by means of a pump 17. The charge also comprises recycled hydrogen supplied through a line. The charge may also be preheated by a heat exchanger 11 upstream of its passage into the convection section, the heat exchanger receiving heat from the reactor effluent, which is discharged in parallel through a line 5 connected to it. The effluent is then directed by a set of appropriate valves 29 to a cooling tower 67, then to a gas/liquid separating flask 68 and finally to a fractionating section 70 which makes it possible to collect the hydrocarbons produced through a line, a gas enriched with hydrogen which may be recycled through a line and the non-converted charge which may be recycled.

The reaction chamber has a reaction cell, as shown in FIG. 1 described above. It also has a regeneration cell arranged substantially symmetrically relative to the axis of the chamber passing through the convection section. The regeneration cell is in fact substantially identical with the hydrocarbon-producing cell, since the two reactors operate alternately, with one operating in hydrocarbon-producing phase while the other operates in catalyst-regenerating phase.

The cell 8 operating in regeneration thus comprises the plurality of tubes 3 described above, arranged in rows with the burners 6 between them. The burners 6 are disposed in layers and adapted to heat the tubes under the regenerating conditions described above. The combustion gases from the burners 6 are directed through a passage 15 to the convection section 13. The tubes contain the catalyst on which coke has been deposited during the preceding, hydrocarbon-producing phase. First the gas used for the purge (nitrogen), supplied through the line a, then a mixture of nitrogen and air (0.5% of oxygen by volume), supplied through the lines (a) and (b), are introduced after being compressed, at the inlet of the regenerator 8 through the line 9 and the valve 28. The tubes are fed in parallel and in the same direction as that in which the charge is introduced. The fixed bed catalyst is at least partly regenerated under appropriate conditions and the combustion effluent is discharged through a line 10 and passes through the heat exchanger 12, which partially preheats the purging gas and regenerating gas. Additional preheating of these gases is carried out in the convection section 13.

The regeneration effluent is then directed by a set of valves 32 to a treatment and separation section (not shown), through the line 10.

In the embodiment already described, one cell operates in olefinic hydrocarbon production while the other operates in regeneration phase. After the time required for the hydrocarbon-producing reaction (about 12 hours) appropriate alternating displacement means 20 allow an alternation to take place, with the reactor 2 passing into regeneration phase while the regenerator 8 passes into hydrocarbon-producing phase.

During the phase required for purging, valves 26 and 28, which together supply the circuit with nitrogen, are open, valves 25 and 27 are closed and valves 30 and 32 for recovering the purge effluent are open while valves 29 and 31 are closed. A phase of reducing the catalyst in $H_2$ may be carried out when it has been regenerated and after the purging phase.

After the purging phase the alternating displacement means open the valve 25 to feed the reactor with the charge comprising recycled hydrogen, and close the valves 26 and 27. These same means close the valves 30 and 31 to let the effluent be discharged through the valve 29, which is open towards the fractionating section 70.

Similarly, the alternating displacement means 20 let the $N_2$/air mixture pass through the open valve 28 to the regeneration cell 8 with the valve 27 closed, while the regeneration effluent is directed to the treatment section through the opening of the valve 32 and the closing of the valve 31.

After another purging phase the displacement means 20 make the reactor 2 become a regenertor. The line 9 for the regenerating gas mixture supplies the reactor through the open valve 26, with the valves 28 and 29 closed, while the regeneration effluent is discharged through the line 5 with the valve 30 open and the valves 29 and 32 closed. The alternating displacement means similarly make the regenerator 8 become a reactor. For this purpose the charge is passed through a line and the open valve 27—with the valves 25 and 28 closed—to the line 9 supplying the reaction tubes, and the effluent from the reaction producing olefinic hydrocarbons is passed to the treatment section 70 through the line 10, with the valve 31 open and the valves 29 and 32 closed.

The alternating displacement means 20 are of course connected to the means 50 for regulating the heating layers, which adjust the heating and thus the fuel feed differently during the olefin-producing, purging and regenerating phases.

The means for heating the reactor 2 or the reactor 8 are regulated and controlled as follows (FIG. 2).

Temperature probes 51, 56 and 57, arranged on the reaction tubes substantially at the level of the various heating layers 6, measure the temperature and pass an electric signal respectively through electric lines 52, 58 and 59 to the control and regulation means 50, which are themselves connected the the alternating displacement means 20. For a specific phase of the olefin-producing reaction for example, the electric signals transmitted by the probes are compared with previously recorded reference values. The means 50 then send response signals through the lines 53, 62 and 63, which respectively regulate the valves 54, 60 and 61 for feeding the fuel supplied, through the lines 55, 65 and 66, which are in turn connected to the fuel feed line 7. These valves feed the heating means 6 according to the reference values and the temperature measured.

The chamber shown has one module containing a reactor or cell operating in olefinic hydrocarbon-producing phase and another reactor operating in regeneration phase, the two reactors being linked by a convection section by means of the passages 14 and 15. The chamber may of course contain a plurality of modules, for example with the two adjacent convection sections having one chimney to discharge the combustion effluent.

It has moreover been specified that the catalyst regeneration could include an oxychlorination stage, which takes place after the combustion stage and before the stage of purging the reaction tubes which precedes the stage of producing olefinic hydrocarbons.

Furthermore, as shown in FIG. 1, the hydrocarbon-producing stage and the regeneration stage are carried out by introducing the charge and the regenerating gas in the same direction (e.g. downwardly). It is however quite possible to introduce the charge in one direction and the regenerating gas in the opposite direction, with the apparatus modified in the spirit of the invention.

What is claimed is:

1. A method of producing olefinic hydrocarbons from a charge comprising aliphatic hydrocarbons with 2 to 6 carbon atoms, by dehydrogenation in at least one reaction chamber, the chamber having a plurality of substantially parallel reaction tubes arranged in rows, each tube containing a fixed bed of catalyst, wherein said method comprises:

a) reacting said charge by circulating said charge, optionally preheated, in the tubes containing the fixed beds of catalyst under dehydrogenation conditions at 500–800° C. and collecting an effluent rich in olefinic hydrocarbons;

b) purging the tubes with at least one inert gas, after reaction phase a), and collecting a purge effluent;

c) regenerating the catalyst in the tubes of said at least one reaction chamber under regenerating conditions, to remove coke deposited on said catalyst during reaction phase a), and recovering a regeneration effluent; and d) purging the tubes with at least one inert gas, after regeneration phase c);

wherein the tubes are heated during reaction phase a) by a plurality of radiant ceramic fiber matrix burners arranged at the periphery of the tubes in layers which are substantially parallel, independent of one another, and substantially perpendicular to the tubes, whereby said burners heat a first part of the tubes, representing 1% to 40% of the length of the tubes, with a heat flow equal to 120% to 300% of the mean heat flow of the reaction chamber, and heat the remaining part of the tubes with a heat flow equal to 20% to 85% of the mean heat flow, so that a constant temperature of the catalyst is substantially maintained, and wherein any combustion fumes emanating from said burners is eventually discharged from the chamber.

2. A method according to claim 1, wherein regenerating gas is fed into said tubes during catalyst regenerating phase c).

3. A method of claim 2, wherein feeding of said charge feed and feeding of regenerating gas are respectively stopped during each of purging phases b) and d), and wherein feeding of fuel and oxidant to said burners is optionally stopped, and the reaction tubes are purged at least once with an inert gas, under flow and temperature conditions whereby the temperature of the catalyst is substantially constant.

4. A method of claim 1, wherein the reaction chamber comprises at least one module having a first and second set of tubes and the reaction phase a) is carried out in the first set of tubes while catalyst-regenerating phase c) is carried out in the second set of tubes and subsequently, circulation in the module is alternated so that reaction phase a) is carried out in the second set of tubes and catalyst-regeneration phase c) is carried out in the first set of tubes.

5. A method of claim 1, wherein catalyst-regenerating phase c) comprises a combustion stage effected by injecting an optionally preheated, inert gas and at least one gas containing 0.1% to 5% of molecular oxygen by volume into said reaction tubes, and heating from 1% to 50% of the high length of said reaction tubes at the feed side with a heat flow equal to 5% to 100% of the mean heat flow of the chamber, under conditions to cause combustion of deposited coke whereby the coke combustion reaction is controlled to maintain the temperature of the catalyst substantially constant.

6. A method of claim 5, wherein catalyst-regenerating phase c) further comprises, subsequent to said combustion stage, an oxychlorination stage effected by passing through the tubes a gas containing molecular oxygen and chlorine or a chlorine compound at a temperature of 450° to 500° C., and, optionally, a calcination stage, subsequent to said oxychlorination stage, effected by passing through the tubes a gas with a higher concentration of oxygen than that used in said combustion stage.

7. A method of claim 1, wherein the charge further comprises fresh or recycled hydrogen.

8. A method of claim 1, wherein the charge further comprises water vapor.

9. A method of claim 1, wherein 1% to 35% of the length of the reaction tubes at the first part is heated with a heat flow 150% to 200% of the mean heat flow, and the remaining part of the reaction tubes is heated with a heat flow from 40% to 75% of the mean heat flow.

10. A method of claim 5, wherein the inert gas used in regeneration phase c) is nitrogen.

11. A method of claim 5, wherein 1% to 35% of the length of the reaction tubes at the first part are heated.

12. A method according to claim 1, wherein the charge is a cut containing propane, and the dehydrogenation reaction is conducted at 600°–700° C.

13. A method according to claim 1, wherein the charge is a cut containing isobutane, and the dehydrogenation reaction is conducted at 550°–650° C.

14. A method according to claim 1, wherein during operation the temperature profile along said tubes is substantially flat.

15. A method according to claim 1, wherein reaction phase a) is performed at a pressure of 0.2–20 bar.

16. A method according to claim 15, wherein reaction phase a) is performed at a pressure of 1–3 bar.

17. A method according to claim 1, wherein space velocity through said tubes is 0.5–20 $h^{-1}$.

18. A method according to claim 2, wherein space velocity through said tubes is 1.5–2.5 $h^{-1}$.

19. A method according to claim 1, wherein said catalyst has a specific surface area of 25–500 $m^2/g$.

20. A method according to claim 1, wherein said catalyst contains at least one metal selected from the group consisting of ruthenium, rhodium, palladium, osmium, iridium and platinum, and at least one promoter selected from the elements of Group VIIB.

21. A method according to claim 20, wherein said catalyst is neutralized by at least one compound containing an alkali metal or alkaline earth metal element.

22. A method according to claim 1, wherein the olefinic hydrocarbons produced by dehydrogenation of aliphatic hydrocarbons comprise propene, butenes, and pentenes.

23. A method according to claim 1, wherein said charge comprises 20%–93% isobutane, 5%–78% n-butane, and 2–5% of C3 and C5 aliphatic hydrocarbons.

24. A method according to claim 1, wherein the dehydrogenation reaction is conducted under conditions whereby 10–70% of the charge is converted per pass with a selectivity for olefins of at least 85%, and the yield of iso- and n-olefins produced per pass is greater than 20%.

25. A method according to claim 1, wherein said catalyst is positioned within a peripheral annual portion of the catalyst tubes, and the charge moves axially through the peripheral annual portion into a central portion for recovery of effluent.

* * * * *

UNITED STATES PATENT AND TRADEMARK OFFICE
CERTIFICATE OF CORRECTION

PATENT NO. : 6,191,332 B1
DATED : February 20, 2001
INVENTOR(S) : Duee et al.

It is certified that error appears in the above-identified patent and that said Letters Patent is hereby corrected as shown below:

<u>Column 10,</u>
Line 60, change "0.1%" to -- 0.01% -- and
Line 61, delete "high".

Signed and Sealed this

Nineteenth Day of March, 2002

Attest:

Attesting Officer

JAMES E. ROGAN
*Director of the United States Patent and Trademark Office*